(12) United States Patent
Duprat et al.

(10) Patent No.: US 9,498,465 B2
(45) Date of Patent: Nov. 22, 2016

(54) TOPICAL COMPOSITIONS IN THE FORM OF A GEL CONTAINING A PARTICULAR SOLUBILIZED RETINOID

(71) Applicant: GALDERMA RESEARCH & DEVELOPMENT, Biot (FR)

(72) Inventors: Agnès Duprat, Mougins (FR); Claire Mallard, Mougins (FR)

(73) Assignee: GALDERMA RESEARCH & DEVELOPMENT, Boit (FR)

( * ) Notice: Subject to any disclaimer, the term of this patent is extended or adjusted under 35 U.S.C. 154(b) by 0 days.

(21) Appl. No.: 14/404,913

(22) PCT Filed: May 30, 2013

(86) PCT No.: PCT/EP2013/061200
§ 371 (c)(1),
(2) Date: Dec. 1, 2014

(87) PCT Pub. No.: WO2013/178759
PCT Pub. Date: Dec. 5, 2013

(65) Prior Publication Data
US 2015/0190371 A1     Jul. 9, 2015

Related U.S. Application Data (60) Provisional application No. 61/654,702, filed on Jun. 1, 2012.

(30) Foreign Application Priority Data

Jun. 1, 2012 (FR) ...................................... 12 55092

(51) Int. Cl.
| | | |
|---|---|---|
| A61K 31/40 | (2006.01) |
| A61K 8/34 | (2006.01) |
| A61K 8/49 | (2006.01) |
| A61K 8/67 | (2006.01) |
| A61Q 19/00 | (2006.01) |
| A61K 8/81 | (2006.01) |
| A61K 8/04 | (2006.01) |

(52) U.S. Cl.
CPC ............... *A61K 31/40* (2013.01); *A61K 8/042* (2013.01); *A61K 8/342* (2013.01); *A61K 8/4913* (2013.01); *A61K 8/4946* (2013.01); *A61K 8/671* (2013.01); *A61K 8/8158* (2013.01); *A61Q 19/00* (2013.01)

(58) Field of Classification Search
None
See application file for complete search history.

(56) References Cited

FOREIGN PATENT DOCUMENTS

FR    2915682 A1    11/2008
WO    2006/066978 A1    6/2006

OTHER PUBLICATIONS

English Translation of International Search Report dated Sep. 18, 2013 corresponding to International Patent Application No. PCT/EP2013/061200, 2 pages.

*Primary Examiner* — Samantha Shterengarts
(74) *Attorney, Agent, or Firm* — Dentons US LLP (57) ABSTRACT

A composition in the form of a gel, preferably hydroglycolic, is described. The composition can include in a physiologically acceptable medium, at least one particular retinoid. Also described, is a method for the preparation thereof and the cosmetic and dermatological use of the same.

47 Claims, 2 Drawing Sheets

TOPICAL COMPOSITIONS IN THE FORM OF A GEL CONTAINING A PARTICULAR SOLUBILIZED RETINOID

CROSS-REFERENCE TO PRIOR APPLICATIONS

This application is a National Stage of PCT/EP2013/061200, filed May 30, 2013, and designating the United States (published Dec. 5, 2013, as WO 2013/178759 A1), which claims priority under 35 U.S.C. §119 to U.S. Provisional Application No. 61/654,702, filed Jun. 1, 2012, and French Patent Application No. 1255092, filed Jun. 1, 2012, each hereby expressly incorporated by reference in its entirety and each assigned to the assignee hereof.

The invention relates to a composition of aqueous gel type, preferably aqueous-glycolic gel type, and which comprises, in a physiologically acceptable medium, at least one retinoid of general formula (I)

wherein
- $R_1$ is a hydrogen atom, an alkyl radical having from 1 to 4 carbon atoms or a —$CF_3$ radical;
- $R_2$ is a hydrogen atom, an alkyl or alkoxy radical having from 1 to 4 carbon atoms or a chlorine atom;
- $R_3$ is a hydrogen atom, or a linear or branched alkyl or alkoxy radical having from 1 to 10 carbon atoms, optionally substituted with a methoxy group;
- $R_4$ is a hydrogen atom or an alkyl radical having from 1 to 3 carbon atoms;
- $R_5$ is a hydrogen atom or an alkyl radical having from 1 to 3 carbon atoms;
- or else $R_4$ and $R_5$ form, together with the —N—C(=Y)— bond, a ring of pyrrolidine, pyrrolidinone, piperidine or piperidinone type;
- Y represents two hydrogen atoms or a heteroatom such as oxygen or sulfur;
- Ar represents a 1,4-phenyl, 2,5-pyridyl, 5,2-pyridyl or 2,5-thiophenyl ring;
- X represents an oxygen atom optionally substituted with an alkyl or alkylamine chain or a C—C single bond;
- A represents a hydrogen atom or the formula below:

wherein
- Q is an oxygen atom or the —NH— bond;
- $R_6$ represents a hydrogen atom, an alkyl radical having from 1 to 6 carbon atoms, a cycloalkyl radical having from 3 to 6 carbon atoms, or a —$C(O)CH_2$ or —$C(O)CH_2CH_3$ radical;
- $R_7$ and $R_7'$ represent, independently of one another, a hydrogen atom or a hydroxyl group, on the condition that $R_7$ and $R_7'$ are not simultaneously a hydroxyl group;
- n is 0, 1, 2, 3, 4 or 5.

These compounds, described in patent EP 1 831 149, are powerful retinoids which modulate the nuclear retinoic acid receptor (RAR), more specifically the gamma subtype of this receptor (RARγ).

RAR receptors activate transcription by binding to DNA sequence elements, called RAR response elements (RAREs), in the form of a heterodimer with retinoid X receptors (called RXRs).

Three subtypes of human RARs have been identified and described: RARα, RARβ et RARγ.

Since RAR-gamma receptors are located in the epidermis, it is important for the release of the compounds described by general formula (I) to take place in this part of the skin in order to have a clinical efficacy.

However, the topical application of retinoids can cause skin irritation, dryness and erythema. Many articles describe this irritant effect, such as the articles by Stucker & al. Skin Res Technol. 2002 May; 8(2):133-40 or by Thielitz & al. Am J Clin Dermatol. 2008; 9(6):369-81.

Many techniques are used to obtain topical preparations for pharmaceutical use containing retinoids, in particular emulsions, for instance patent EP-826366 which describes emulsions that can contain retinoids, or else patent EP-989846 which describes emulsions containing retinoids and at least one emulsifier.

However, emulsifiers belong to the chemical family of amphiphilic molecules which are often irritant. Emulsifier-free compositions are as a result less irritant than compositions containing emulsifier.

Not using emulsifier in compositions containing retinoids would therefore make it possible to limit the skin irritation caused by the presence of molecules of this class.

The prior art describes O/W emulsions with or without emulsifier. Mention may in particular be made of U.S. Pat. No. 5,851,538 which describes formulations with or without emulsifier with porous microspheres containing a virtually continuous network of pores open to the exterior and comprising retinoids.

There is consequently a need to have stable and well-tolerated pharmaceutical compositions containing compounds described by general formula (I).

The development of pharmaceutical forms of aqueous-glycolic gel type which generally do not contain emulsifier will therefore provide an advantage in terms of skin tolerance.

According to the FDA, a gel is a semi-solid pharmaceutical form which contains a gelling agent conferring consistency on a colloidal dispersion or solution. An aqueous-glycolic gel is therefore a gel according to this definition, the gelled phase of which contains water and one or more glycols.

A first subject according to the invention relates to a pharmaceutical composition comprising at least one compound of general formula (I)

wherein $R_1$ is a hydrogen atom, an alkyl radical having from 1 to 4 carbon atoms or a —$CF_3$ radical;

$R_2$ is a hydrogen atom, an alkyl or alkoxy radical having from 1 to 4 carbon atoms or a chlorine atom;

$R_3$ is a hydrogen atom, or a linear or branched alkyl or alkoxy radical having from 1 to 10 carbon atoms, optionally substituted with a methoxy group;

$R_4$ is a hydrogen atom or an alkyl radical having from 1 to 3 carbon atoms;

$R_5$ is a hydrogen atom or an alkyl radical having from 1 to 3 carbon atoms;

or else $R_4$ and $R_5$ form, together with the —N—C(=Y)— bond, a ring of pyrrolidine, pyrrolidinone, piperidine or piperidinone type;

Y represents two hydrogen atoms or a heteroatom such as oxygen or sulfur;

Ar represents a 1,4-phenyl, 2,5-pyridyl, 5,2-pyridyl or 2,5-thiophenyl ring;

X represents an oxygen atom optionally substituted with an alkyl or alkylamine chain or a C—C single bond;

A represents a hydrogen atom or the formula below:

wherein

Q is an oxygen atom or the —NH— bond;

$R_6$ represents a hydrogen atom, an alkyl radical having from 1 to 6 carbon atoms, a cycloalkyl radical having from 3 to 6 carbon atoms, or a —$C(O)CH_2$ or —$C(O)CH_2CH_3$ radical;

$R_7$ and $R_7'$ represent, independently of one another, a hydrogen atom or a hydroxyl group, on the condition that $R_7$ and $R_7'$ are not simultaneously a hydroxyl group;

n is 0, 1, 2, 3, 4 or 5;

water, at least one gelling agent, at least one hydrophilic solvent of the compound of formula (I) and at least one hydrophilic cosolvent of the compound of formula (I).

Preferentially, the composition is an aqueous-glycolic gel characterized in that the active agent of general formula (I) is solubilized.

A second subject according to the invention relates to a pharmaceutical composition as described above, for use as a medicament.

A third subject according to the invention relates to a pharmaceutical composition as described above, for use in the treatment of pathological conditions such as:

1) dermatological conditions associated with a keratinization disorder relating to cell differentiation and proliferation, in particular for treating common acne, comedonal acne, polymorphic acne, acne rosacea, nodulocystic acne, acne conglobata, senile acne, secondary acne such as solar acne, acne medicamentosa or occupational acne;

2) keratinization disorders, in particular ichthyosis, ichthyosiform conditions, lamellar ichthyosis, Darier's disease, palmoplantar keratoderma, leukoplakia, pityriasis rubra pilaris and leukoplakiform conditions, cutaneous or mucosal (buccal) lichen;

3) dermatological conditions with an inflammatory immunoallergic component, with or without a cell proliferation disorder, and in particular all forms of psoriasis, whether cutaneous, mucosal or ungual, and even psoriatic arthritis, or else atopic dermatitis and the various forms of eczema;

4) skin disorders caused by exposure to UV radiation, and also for repairing or combating skin aging, whether it is photo-induced or chronological, or for reducing actinic keratoses and pigmentations, or any pathological conditions associated with chronological or actinic aging, such as xerosis, pigmentations and wrinkles;

5) any condition associated with benign dermal or epidermal proliferations, whether or not they are of viral origin, such as common warts, flat warts, molluscum contagiosum and epidermodysplasia verruciformis, or oral or florid papillomatoses;

6) dermatological disorders such as immune dermatoses, for instance lupus erythematosus, bullous immune diseases and collagen diseases, such as scleroderma;

7) stigmata of epidermal and/or dermal atrophy induced by local or systemic corticosteroids, or any other form of cutaneous atrophy;

8) healing disorders, or for preventing or repairing stretch marks, or else for promoting healing;

9) in the treatment of any condition of fungal origin at the cutaneous level, such as tinea pedis and tinea versicolor;

10) pigmentation disorders, such as hyperpigmentation, melasma, hypopigmentation or vitiligo;

11) cutaneous or mucosal cancerous or precancerous conditions, such as actinic keratoses, Bowen's disease, in-situ carcinomas, keratoacanthomas and skin cancers such as basal cell carcinoma (BCC), squamous cell carcinoma (SCC) and cutaneous lymphomas such as T lymphoma.

A fourth subject according to the invention relates to a method for preparing a pharmaceutical composition as previously described and comprising the following steps:

a) Solubilization of the hydrophilic additives in water with stirring.

b) Solubilization, with stirring, of the retinoid of general formula (I) in the preferred solvent.

c) Addition of ethanol and propylene glycol.

d) Gelling of the aqueous phase by adding the gelling agent.

e) Addition of the active phase (b) to (d).

A fifth subject according to the invention relates to compositions of aqueous-glycolic gel type comprising a compound of general formula (I)

and at least one polyacrylamide gelling agent, characterized in that the maximum amount of active ingredient absorbed in the dermis and the epidermis 16 hours after application is between 5 ng/cm² and 15 ng/cm².

A sixth subject according to the invention relates to compositions of aqueous-glycolic gel type comprising a compound of general formula (I)

and at least one polyacrylamide gelling agent, characterized in that the maximum amount of active ingredient absorbed in the epidermis is obtained between 1 and 6 hours after application.

The invention will be described in greater detail in the description and the examples which follow, and also in the appended figures in which.

DETAILED DESCRIPTION OF THE INVENTION

For the purposes of ease of reading, general formula (I) and compound A will be considered, in the rest of the text, as being described as follows:

General Formula (I):

wherein
$R_1$ is a hydrogen atom, an alkyl radical having from 1 to 4 carbon atoms or a —$CF_3$ radical;
$R_2$ is a hydrogen atom, an alkyl or alkoxy radical having from 1 to 4 carbon atoms or a chlorine atom;
$R_3$ is a hydrogen atom, or a linear or branched alkyl or alkoxy radical having from 1 to 10 carbon atoms, optionally substituted with a methoxy group;
$R_4$ is a hydrogen atom or an alkyl radical having from 1 to 3 carbon atoms;
$R_5$ is a hydrogen atom or an alkyl radical having from 1 to 3 carbon atoms;
or else $R_4$ and $R_5$ form, together with the —N—C(=Y)— bond, a ring of pyrrolidine, pyrrolidinone, piperidine or piperidinone type;
Y represents two hydrogen atoms or a heteroatom such as oxygen or sulfur;
Ar represents a 1,4-phenyl, 2,5-pyridyl, 5,2-pyridyl or 2,5-thiophenyl ring;
X represents an oxygen atom optionally substituted with an alkyl or alkylamine chain or a C—C single bond;
A represents a hydrogen atom or the formula below:

wherein
Q is an oxygen atom or the —NH— bond;
$R_6$ represents a hydrogen atom, an alkyl radical having from 1 to 6 carbon atoms, a cycloalkyl radical having from 3 to 6 carbon atoms, or a —$C(O)CH_2$ or —$C(O)CH_2CH_3$ radical;
$R_7$ and $R_7'$ represent, independently of one another, a hydrogen atom or a hydroxyl group, on the condition that $R_7$ and $R_7'$ are not simultaneously a hydroxyl group;
n is 0, 1, 2, 3, 4 or 5.

Compound A: as being 3"-tert-butyl-4'-(2-hydroxyethoxy)-4"-pyrrolidin-1-yl[1,1';3',1"]terphenyl-4-carboxylic acid.

In the light of the physicochemical characteristics of the active agent, the applicant has had to face a certain number of constraints regarding the use of the compounds described by general formula (I). These compounds:
 are insoluble in water,
 are particularly soluble in two solvents determined from the pre-formulation studies as described in example 1,
 are stable in only two cosolvents of compound A, determined from the pre-formulation studies as described in example 1.

In addition, the maximum concentrations of the main solvents in the pharmaceutical compositions are preferably limited in order to optimize tolerance. Thus, the composition according to the invention preferably contains a maximum amount of 1% by weight of phenoxyethanol. It also preferably contains a maximum amount of 30% percent by weight of ethanol.

A first subject according to the present invention relates to pharmaceutical compositions containing at least one active agent which is a compound of general formula (I), these compositions being in the form of an aqueous gel, preferably an aqueous-glycolic gel, and the active agent being solubilized in said compositions.

Such gels exhibit good physical and chemical stability, a rapid penetration speed and a high level of penetration into the epidermis.

According to the FDA, a gel is a semi-solid pharmaceutical form which contains a gelling agent conferring consistency on a colloidal dispersion or solution. An aqueous-glycolic gel is therefore a gel according to this definition, the gelled phase of which contains water and one or more glycols.

In the invention, the compositions contain the active agent described by general formula (I) at concentrations preferably ranging from 0.00001% to 1% by weight, more preferentially from 0.0001% to 0.1% by weight and more preferentially from 0.001% to 0.1% by weight, relative to the total weight of the composition.

Preferentially, the active agent described by general formula (I) is compound A.

In the invention, the compositions contain at least one hydrophilic solvent of compound A.

The term "solvent" is intended to mean a liquid which has the property of dissolving, diluting or extracting substances without causing chemical modification of these substances and without itself being modified.

According to the invention, the hydrophilic solvent is such a liquid, in which the compounds of general formula (I) (and more particularly compound A) have a solubility, at ambient temperature and atmospheric pressure, greater than or equal to 0.1% by weight.

In the light of the pre-formulation results (example 1), the hydrophilic solvent can be advantageously selected from the list comprising methylpyrrolidone, ethoxydiglycol, benzyl alcohol, polyethylene glycol 400, phenoxyethanol and ethanol.

The solvent preferentially comprises the phenoxyethanol sold, for example, under the name phenoxetol by Clariant, and which can be used in a content ranging from 0.2% to 5% by weight and more preferentially from 0.5% to 2% by weight, relative to the total weight of the composition. The solvent can also comprise ethanol which can be used from 5% to 50% by weight and preferentially from 15% to 30% by weight, relative to the total weight of the composition.

In the invention, the compositions contain at least one cosolvent.

The term "cosolvent" is intended to mean a substance which acts as a solvent in combination with another substance.

In the light of the pre-formulation results (example 1), the cosolvent can be chosen from glycols, such as monopropylene glycol and dipropylene glycol, and can be used in the contents ranging from 2% to 50% by weight and preferentially from 10% to 40% by weight, relative to the total weight of the composition.

In the invention, the compositions contain at least one gelling agent.

The term "gelling agent" is intended to mean a polymer compound capable of conferring on the composition the texture of a gel.

The gelling agent(s) can in particular be chosen from polymers of vegetable origin, gums, pectins, cellulose and its derivatives, polymers of microbiological origin, such as xanthan gum, and gelling polymers of synthetic origin.

By way of nonlimiting example of gelling agents which can be part of the compositions, mention may be made of the acrylates/C10-30 alkyl acrylate crosspolymer sold under the name Pemulen TR-1 or Pemulen TR-2 by the company Lubrizol, gelling agents of the polyacrylamide family, such as the sodium acrylamide/acryloyldimethyl taurate copolymer/isohexadecane/polysorbate 80 mixture sold under the name Simulgel 600PHA by the company SEPPIC, and the polyacrylamide/isoparaffin C13-14/laureth-7 mixture sold under the name Sepigel 305 by the company SEPPIC, the carbomers sold under the name Ultrez 20®, Ultrez 10®, Carbopol 1382® or Carbopol ETD2O2ONF®, Carbopol 981 or else Carbopol 980 by the company Lubrizol, polysaccharides with, by way of nonlimiting examples, xanthan gum, such as Xantural180® sold by the company Kelco, the gellan gum sold under the name Kelcogel by the company Kelco, guar gum, cellulose and its derivatives, such as the microcrystalline cellulose and sodium carboxymethylcellulose sold under the name Avicel CL-611 by the company FMC Biopolymer, hydroxypropylmethylcellulose, in particular the product sold under the name Methocel E4M premium by the company Dow Chemical, or hydroxyethylcellulose, in particular the product sold under the name Natrosol HHX 250® by the company Ashland, sodium carboxymethylcellulose, in particular Blanose cellulose gum 7F sold by the company Ashland, the family of aluminum magnesium silicates, such as Veegum K sold by the company Vanderbilt, the family of acrylic polymers coupled to hydrophobic chains, such as the PEG-150/decyl/SMDI copolymer sold under the name Aculyn 44 (polycondensate comprising at least as elements a polyethylene glycol comprising 150 or 180 mol of ethylene oxide, decyl alcohol and methylenebis(4-cyclohexylisocyanate) (SMDI), at 35% by weight in a mixture of propylene glycol (39%) and water (26%)), the family of modified starches, such as the modified potato starch sold under the name Structure Solanace, or else mixtures thereof, the family of carrageenans, in particular divided up into four major families: κ, λ, β, ω, such as the Viscarin® products and the Gelcarin® products sold by the company IMCD.

Preferentially, a gelling agent of polyacrylamide type such as Simulgel 600 PHA® is used, at concentrations ranging from 0.005% to 5% by weight and preferentially ranging from 1% to 4% by weight, alone or combined with at least one of the gelling agents mentioned above at concentrations ranging from 0.005% to 3% by weight.

In the invention, the compositions can contain additives among which mention may be made of the following categories (used alone or in combination):

Preserving agents, such as methyl paraben, propyl paraben, benzalkonium chloride, phenoxyethanol sold under the name phenoxetol by Clariant, benzyl alcohol sold under the name benzyl alcohol by Merck, potassium sorbate sold under the name potassium sorbate by VWR, benzoic acid sold under the name benzoic acid by VWR, 2-bromo-2-nitropropane-1,3-diol sold under the name Bronopol by Jan Dekker International, chlorhexidine sold under the name Chlorhexidine digluconate 20% solution by Arnaud Pharmacie, chlorocresol and its derivatives, sodium benzoate sold under the name Probenz SP by Unipex, ethyl alcohol and diazolidinylurea. These preservatives can be used alone or in combination in order to efficiently protect the formulae against any bacterial contamination.

Agents for improving the properties of the formulae on application, such as cyclomethicone (St-Cyclomethicone 5NF) or dimethicone (Q7 9120 silicon fluid having a viscosity of 20 cst to 12500 cst from Dow Corning).

Chelating agents such as EDTA (ethylenediaminetetraacetic acid) and its derivatives or salts, dihydroglycerol, citric and tartaric acids, the gluconolactone sold under the name glucono-delta-lactone SG by Jungbun­zlauer, or mixtures thereof.

Antioxidants such as vitamin E and its derivatives, for instance DL-alpha-tocopherol or tocopheryl acetate from Roche, vitamin C and its derivatives, for instance ascorbyl palmitate from Roche, the butylhydroxytolu­ene sold under the name Nipanox BHT by Clariant.

Soothing agents and/or anti-irritants, such as the PPG-12/SMDI copolymer sold by the company Bertek Phar­maceuticals under the trade name Polyolprepolymer-2, glycyrrhetinic acid or its derivatives, for instance Enox­olone sold by the company BASF, hyaluronic acid as it is or in its sodium hyaluronate form sold under the trade name Hyal. Na PWD PH 15-41-45 by the company Contipro, the allantoin sold under the name Ronacare Allantoine by Merck.

Any other additives normally used in the pharmaceutical and cosmetics field which make it possible to confer specific properties on said preparation.

The composition according to the invention advanta­geously has the following general composition, the percent­ages being expressed by weight relative to the total weight of the composition:

from 0.00001% to 1% by weight, preferentially from 0.0001% to 0.1% by weight, more preferably from 0.001% to 0.1% by weight, of compound A, water, from 0.005% to 10% by weight and preferentially from 1% to 4% by weight of gelling agent, from 0.2% to 50% by weight and preferentially from 0.5% to 30% by weight of hydrophilic solvent, from 2% to 50% by weight and preferentially from 10% to 40% by weight of cosolvent, optionally, from 0 to 15% by weight and preferentially from 0.1% to 10% by weight of one or more additives.

Another subject according to the invention relates to a method for preparing a pharmaceutical composition as pre­viously described and comprising the following steps:

A) Preparation of the aqueous phase: solubilize the hydro­philic additives in water with stirring.

B) Preparation of the active phase:

Solubilize, with stirring, compound A in the hydrophilic solvent (for example, phenoxyethanol), if necessary under hot conditions.

At ambient temperature, add the cosolvent(s) (for example, ethanol and propylene glycol).

C) Mixing of the two phases:

Gel the aqueous phase by adding the thickener (for example, Simulgel 600PHa) with stirring, then add the active phase.

Once this mixture is homogeneous, add the cyclomethi­cone-5 (if present in the formula) with stirring.

EXAMPLES

Example 1

Pre-Formulation

In order to produce an aqueous-glycolic gel containing an amount of ethanol of less than 30%, in which compound A is solubilized, pre-formulation studies were carried out in order to reveal the excipients enabling good solubilization and also good stability of the active agent.

(1) List of the hydrophilic excipients or mixture of hydrophilic excipients in which maximum solubility was determined by HPLC:

| Trade name | INCI name | Maximum solubility as % |
|---|---|---|
| Pharmasolve | Methyl Pyrolidone | 4.84 |
| Transcutol | Ethoxy diglycol | 4.17 |
| Benzyl Alcohol | Benzoyl Alcohol | 2.3880 |
| PEG 400 | Peg-8 | 1.52 |
| Phenoxetol | Phenoxyethanol | 1.957 |
| Ethanol 95-96% | Ethanol | 0.92 |
| Hydrolite 5P | Pentylene glycol | 0.482 |
| Arlasolve DMI | Dimethyl Isosorbide | 0.4 |
| Hexylene Glycol | Hexylene Glycol | 0.4 |
| Dipropylene Glycol Care | Dipropylene Glycol | 0.4 |
| Propylene Glycol | Propylene Glycol | 0.111 |
| Glycerine | Glycerin | 0.002 |

This study shows that 6 solvents can be considered to be "principal solvents" of compound A (Pharmasolve, Transcu­tol, benzyl alcohol, PEG 400, Phenoxetol and ethanol), it being possible for the others to be used as "cosolvents", apart from the glycerine, in which compound A is virtually insoluble.

(2) Stability of compound A in its principal solvents, determined by HPLC

| Excipients | | Compound A | |
|---|---|---|---|
| Trade name | INCI name | % | Stability results |
| Pharmasolve | Methyl Pyrolidone | 0.03% | Unstable |
| Transcutol | Ethoxy diglycol | 0.03% | Unstable |
| Benzyl Alcohol | Benzoyl Alcohol | 0.01% | Unstable |
| PEG 400 | Poly Ethylene Glycol | 0.3% | Unstable |
| Phenoxetol | Phenoxyethanol | 0.05% | Stable |
| Ethanol 95-96% | Ethanol | 0.005% | Stable |

These stability studies show that, among the "principal solvents" identified, compound A is stable only in phenoxy­ethanol and ethanol.

(3) Stability of compound A in its cosolvents, determined by HPLC

| Excipients | | COMPOUND A | Stability |
|---|---|---|---|
| Trade name | INCI name | % | results |
| Hydrolite 5P | Pentylene glycol | 0.03% | Unstable |
| Arlasolve DMI | Dimethyl Isosorbide | 0.03% | Unstable |
| Hexylene Glycol | Hexylene Glycol | 0.001% | Unstable |
| Dipropylene Glycol Care | Dipropylene Glycol | 0.3% | Stable |
| Propylene Glycol | Propylene Glycol | 0.05% | Stable |

These stability studies show that, among the "cosolvents" identified, compound A is stable only in dipropylene glycol and propylene glycol.

Example 2

Formulations

In the following examples, the formulae produced are characterized at T0. The physical and chemical stability of the formulations is determined after storage at ambient temperature (AT) and +40° C. after T+1 Month and/or T+2 Months or T+3 Months or T+6 Months. The material and the methods used for these characterizations are described below.

Chemical Assaying of Compound A:
Material: HPLC
Expression of the results: the titer of the active agent is expressed as relative % with respect to the initial % performed at T0. The limits set for good stability are 95%-105%.

Macroscopic Observation:
The macroscopic observation makes it possible to guarantee the physical integrity of the products at T0 and afterwards stability.

Microscopic Observation:
The microscopic observation makes it possible to evaluate the good solubilization of COMPOUND A as early as T0, the non-recrystallization over time and also the size of the globules of the oily phase.
Material: Zeiss Axio microscope pH:
Material: Mettler Toledo SevenMulti pH meter
Method: Measurements carried out at ambient temperature after stabilization of all the samples for 24 h in a chamber at 25° C.

Viscosity:
The viscosity measurement makes it possible to evaluate the consistency of the formulae produced.
Material: Brookfield RV DVII+Pro
Method: Measurements carried out at ambient temperature after stabilization of all the samples for 24 h in a chamber at 25° C. The value is read after 1 minute. The choice of the spindle and of the speed will be described in each composition example. The values obtained are expressed in centipoises (Cps).

Centrifugation:
The centrifugation makes it possible to evaluate the resistance of the formulae to a mechanical stress.
Material: Galaxy 14D VWR
Method: 30 minutes at 5000 rpm
A result which complies signifies that there is neither phase separation nor exudate.

Formula No. 1

| TRADE NAME | INCI NAME | % |
|---|---|---|
| COMPOUND A | COMPOUND A | 0.010 |
| PROPYLENE GLYCOL | Propylene glycol | 38.000 |
| ETHANOL 95-96% | Ethanol | 30.000 |
| RONACARE ALLANTOIN | Allantoin | 0.200 |
| SIMULGEL 600 PHA | Acrylamide, AMPS Copolymer Dispersion 40%/Isohexadecane/polysorbate 80 | 4.000 |
| ST-CYCLOMETHICONE 5NF | Cyclopentasiloxane | 2.000 |
| PHENOXETOL | Phenoxyethanol | 1.000 |
| PURIFIED WATER | Purified water | QS 100.000 |

| CHARACTERIZATION AT T0 | MACROSCOPIC APPEARANCE | Shiny, smooth, white gel |
|---|---|---|
| | MICROSCOPIC APPEARANCE | Absence of crystals. |
| | pH | Not able to be done |
| | VISCOSITY | Not done |
| | CENTRIFUGATION | Complies |

| MONITORING OF STABILITY | | 1 Month | 2 Months | 3 Months | 6 Months |
|---|---|---|---|---|---|
| Microscopic appearance | | Complies, no recrystallization | Complies, no recrystallization | Complies, no recrystallization | Complies, no recrystallization |
| Macroscopic appearance | | Complies | Complies | Complies | Complies |
| Chemical stability | Assay Compound A initial % | AT 40° C. | 98.40 98.30 | 98.70 98.60 | 97.50 96.40 | 101.210 100.50 |

These results show good physical and chemical stability of the active agent and of the composition as a whole over time.

Formula No. 2

| TRADE NAME | INCI NAME | % |
|---|---|---|
| COMPOUND A | COMPOUND A | 0.010 |
| PROPYLENE GLYCOL | Propylene glycol | 40.000 |
| ETHANOL 95-96% | Ethanol | 30.000 |
| RONACARE ALLANTOIN | Allantoin | 0.200 |
| SIMULGEL 600 PHA | Acrylamide, AMPS Copolymer Dispersion 40%/Isohexadecane/polysorbate 80 | 4.000 |
| PHENOXETOL | Phenoxyethanol | 1.000 |
| PURIFIED WATER | Purified water | QS 100.000 |

| CHARACTERIZATION AT T0 | MACROSCOPIC APPEARANCE | Shiny, smooth, white gel |
|---|---|---|
| | MICROSCOPIC APPEARANCE | Absence of crystals. |
| | pH | Not able to be done |
| | VISCOSITY | Not done |
| | CENTRIFUGATION | Complies |

-continued

| MONITORING OF STABILITY | | 1 Month | 2 Months | 3 Months | 6 Months |
|---|---|---|---|---|---|
| Microscopic appearance | | Complies, no recrystallization | Complies, no recrystallization | Complies, no recrystallization | Complies, no recrystallization |
| Macroscopic appearance | | Complies | Complies | Complies | Complies |
| Chemical stability | Assay COMPOUND A initial % | AT 40° C. | 99.90 97.50 | 101.80 99.60 | 103.20 96.80 | 99.70 95.90 |

These results show good physical and chemical stability of the active agent and of the composition as a whole over time.

Formula No. 3

| TRADE NAME | INCI NAME | % |
|---|---|---|
| COMPOUND A | COMPOUND A | 0.010 |
| PROPYLENE GLYCOL | Propylene glycol | 40.000 |
| ETHANOL 95-96% | Ethanol | 20.000 |
| RONACARE ALLANTOIN | Allantoin | 0.200 |
| SIMULGEL 600 PHA | Acrylamide, AMPS Copolymer Dispersion 40%/Isohexadecane/polysorbate 80 | 3.000 |
| ST-CYCLOMETHICONE 5NF | Cyclopentasiloxane | 2.000 |
| PHENOXETOL | Phenoxyethanol | 1.000 |
| PURIFIED WATER | Purified water | QS 100.000 |

| CHARACTERIZATION AT T0 | MACROSCOPIC APPEARANCE | Shiny, smooth, white gel |
|---|---|---|
| | MICROSCOPIC APPEARANCE | Absence of crystals. |
| | pH | Not able to be done |
| | VISCOSITY | Not done |
| | CENTRIFUGATION | Complies |

| MONITORING OF STABILITY | | 1 Month | 2 Months | 3 Months | 6 Months |
|---|---|---|---|---|---|
| Microscopic appearance | | Complies, no recrystallization | Complies, no recrystallization | Complies, no recrystallization | Complies, no recrystallization |
| Macroscopic appearance | | Complies | Complies | Complies | Complies |
| Chemical stability | Assay COMPOUND A initial % | AT 40° C. | 100.10 101.10 | 96.60 95.50 | 97.90 97.00 | 97.10 93.90 |

These results show good physical and chemical stability of the active agent and of the composition as a whole over time.

Formula No. 4

| TRADE NAME | INCI NAME | % |
|---|---|---|
| COMPOUND A | COMPOUND A | 0.010 |
| DIPROPYLENE GLYCOL CARE | Dipropylene glycol | 40.000 |
| ETHANOL 95-96% | Ethanol | 20.000 |
| RONACARE ALLANTOIN | Allantoin | 0.200 |
| SIMULGEL 600 PHA | Acrylamide, AMPS Copolymer Dispersion 40%/Isohexadecane/polysorbate 80 | 3.000 |
| ST-CYCLOMETHICONE 5NF | Cyclopentasiloxane | 2.000 |
| PHENOXETOL | Phenoxyethanol | 1.000 |
| PURIFIED WATER | Purified water | QS 100.000 |

Formula No. 5:

| TRADE NAME | INCI NAME | % |
|---|---|---|
| COMPOUND A | COMPOUND A | 0.020 |
| DIPROPYLENE GLYCOL CARE | Dipropylene glycol | 40.000 |
| ETHANOL 95-96% | Ethanol | 20.000 |
| RONACARE ALLANTOIN | Allantoin | 0.200 |
| SIMULGEL 600 PHA | Acrylamide, AMPS Copolymer Dispersion 40%/Isohexadecane/polysorbate 80 | 3.000 |
| PHENOXETOL | Phenoxyethanol | 2.000 |
| PURIFIED WATER | Purified water | QS 100.000 |

Formula No. 6:

| TRADE NAME | INCI NAME | % |
|---|---|---|
| COMPOUND A | COMPOUND A | 0.005 |
| DIPROPYLENE GLYCOL CARE | Dipropylene glycol | 40.000 |
| ETHANOL 95-96% | Ethanol | 20.000 |
| SIMULGEL 600 PHA | Acrylamide, AMPS Copolymer Dispersion 40%/Isohexadecane/polysorbate 80 | 3.000 |
| ST-CYCLOMETHICONE 5NF | Cyclopentasiloxane | 2.000 |
| PURIFIED WATER | Purified water | QS 100.000 |

Formula No. 7:

| TRADE NAME | INCI NAME | % |
|---|---|---|
| COMPOUND A | COMPOUND A | 0.005 |
| PROPYLENE GLYCOL | Propylene Glycol | 40.000 |
| ETHANOL 95-96% | Ethanol | 20.000 |
| RONACARE ALLANTOIN | Allantoin | 0.200 |
| SIMULGEL 600 PHA | Acrylamide, AMPS Copolymer Dispersion 40%/Isohexadecane/polysorbate 80 | 3.000 |
| PHENOXETOL | Phenoxyethanol | 1.000 |
| PURIFIED WATER | Purified water | QS 100.000 |

Formula No. 8:

| TRADE NAME | INCI NAME | % |
|---|---|---|
| COMPOUND A | COMPOUND A | 0.010 |
| DIPROPYLENE GLYCOL CARE | Dipropylene glycol | 40.000 |
| ETHANOL 95-96% | Ethanol | 20.000 |
| RONACARE ALLANTOIN | Allantoin | 0.200 |
| SIMULGEL 600 PHA | Acrylamide, AMPS Copolymer Dispersion 40%/Isohexadecane/polysorbate 80 | 4.000 |
| ST-CYCLOMETHICONE 5NF | Cyclopentasiloxane | 1.000 |
| PURIFIED WATER | Purified water | QS 100.000 |

Formula No. 9:

| TRADE NAME | INCI NAME | % |
|---|---|---|
| COMPOUND A | COMPOUND A | 0.01 |
| DIPROPYLENE GLYCOL CARE | Dipropylene glycol | 30.000 |
| ETHANOL 95-96% | Ethanol | 15.000 |
| RONACARE ALLANTOIN | Allantoin | 0.200 |
| SIMULGEL 600 PHA | Acrylamide, AMPS Copolymer Dispersion 40%/Isohexadecane/polysorbate 80 | 3.000 |
| ST-CYCLOMETHICONE 5NF | Cyclopentasiloxane | 1.000 |
| PURIFIED WATER | Purified water | QS 100.000 |

Example 3

Characterization of the Formulations by Means of Cutaneous Penetration Studies on Human Skin The cutaneous penetration studies make it possible to characterize the formulations, and to demonstrate parameters specific to each of the formulations.

Two types of cutaneous penetration studies on human skin ex vivo were carried out.

In these studies, compound A corresponds to 3"-tert-butyl-4'-(2-hydroxyethoxy)-4"-pyrrolidin-1-yl[1,1';3',1"]terphenyl-4-carboxylic acid.

The reference gel being described as follows:

| Constituents | % |
|---|---|
| Compound A | 0.01 |
| Propylene Glycol | 30.00 |
| Ethanol 95-96% | 67.99 |
| Klucel HF Pharma | 2.00 |

In these 2 studies, the "optimized gel" composition corresponding to formula 3 is evaluated in comparison to a "reference gel" composition.

1—"Single Time" Cutaneous Penetration Study:

In this study, the formula is applied for 16 h at the surface of the skin. At the end of the application, compound A is quantified in the various skin compartments: stratum corneum, epidermis, dermis and receiving liquid according to a validated bioanalysis method.

The details of the cutaneous application are given in the table below.

| Skin: 3 donors, 2 samples per donor | |
|---|---|
| Source | Whole abdominal human skin |
| Thickness | 0.79-1.22 mm |
| Age | 39-64 years old. |
| Franz cells | 2 cm$^2$ |
| Receiving liquid volume | 3ml |
| Barrier function | Evaluated by determination of insensible water loss, acceptable unless contraindication |
| Formulations | |
| A: Reference gel containing 100 µg/g compound A | B: Gel (aqueous-glycolic) containing 100 µg/g compound A corresponding to formula 3 |
| Application | |
| Application | ~2 mg/cm$^2$ |
| Amount of active agent applied | 142~241 ng/cm$^2$ |
| Exposure time | 16 h |
| Samples taken up | |
| Washing of donor compartment Kleenex (for removing the surplus product) 1st strip | "Excess"/Dose nonabsorbed |
| Stratum corneum (2-15 strips max) | Balance of masses |
| Epidermis | Total Skin, Total penetration |
| Dermis | |
| Receiving Liquid | Dose absorbed |

The bioanalysis was carried out by positive electrospray ionization tandem mass spectrometry, and using a Xevo apparatus (Waters). The quantification limit for compound A is 1 ng/ml.

The LC/MS/MS conditions developed made it possible to detect up to 0.1% of the dose applied in each of the compartments (dose nonabsorbed, stratum, epidermis, dermis and receiving liquid).

The technical conditions are given in the table below.

| LC Column | Hypersil gold 50 × 2.1 mm (UPLC) |
|---|---|
| Mobile Phase | Phase A: ACN + 0.1% Formic Acid |
| | Phase B: H$_2$O + 0.1% Formic acid |
| Washing of needle | ACN |
| Washing of septum | ACN/H$_2$O 50:50 |

-continued

|  | T (min) | flow rate | % A | % B | Curve |
|---|---|---|---|---|---|
| Gradient | 1. Initial | 0.700 | 15.0 | 85.0 | 0 |
|  | 2. 2.5 | 0.700 | 90.0 | 10.0 | 6 |
|  | 3. 3.20 | 0.700 | 90.0 | 10.0 | 6 |
|  | 4. 3.25 | 0.700 | 15.0 | 85.0 | 6 |

Column temperature
MSMS detection  ESI+ MRM (Positive Electrospray)

|  | Reaction Channel | Dwell (secs) | Voltage (cone) | Col. Energy | Tr (min) | Compound |
|---|---|---|---|---|---|---|
|  | 1: 460.26 > 318.20 | 0.100 | 50.0 | 40.0 | 1.58 | Compound A |
|  | 1: 464.06 > 372.10 | 0.100 | 55.0 | 40.0 | 1.58 | Deuterated Internal Reference |

Injection Volume  5 µl
Run time  4 minutes a—Profile of Distribution in the Various Compartments (Qualitative Data):

The distribution between the various compartments is of the same type for the 2 formulae evaluated: accumulation in the stratum corneum and lower degree of penetration in the epidermis. Compound A is not detected in the receiving liquid and is very weakly present in the dermis.

b—Values for Penetration in the Epidermis+Dermis Compartment:

The penetration values for the optimized gel (example 3) containing 100 µg/g (0.01%) of compound A are around 9 ng/cm². The levels of penetration of compound A after application of the optimized gel (example 3) tend to be higher than those obtained after application of the reference gel.

Figure 1:
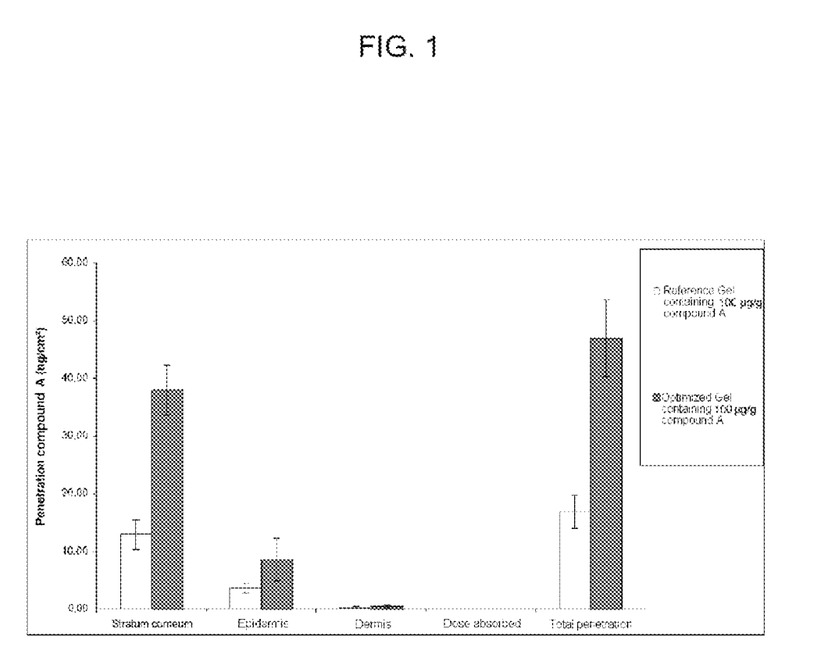
FIGS. 1 and 2 show the results of a study of the kinetics of penetration into the epidermis of a composition according to the invention and of a reference gel.

1—Penetration Kinetics Study—FIG. 1:

In this type of study, the penetration of the active agent is quantified in each compartment of the skin after 0.5 h, 1 h, 3 h, 6 h and 24 h of application. Kinetics of penetration into each compartment are then determined and characterized.

The details of the cutaneous application are given in the table below:

| Skin | 3 donors, 2 samples per donor per time, n = 6 |
|---|---|
| Source | Dermatomed abdominal human skin from a corpse |
| Thickness | 500 µm |
| Age | Not Communicated |
| Franz cells | 1-2 cm² |
| Receiving Liquid Volume | Not Communicated |
| Barrier Function | Evaluated using tritiated water |
| Products |  |
| Reference gel 100 µg/g | Optimized gel (aqueous-glycolic gel) 100 µg/g corresponding to formula 3 |
| Application of Formula | ~2 mg/cm² |
| Amount of active agent applied | Between 100-200 ng/cm² |
| Exposure time | Up to 24 h |
| Samples taken up Exposure time | 0.5, 1, 3, 6, 24 h |
| Washing of donor compartment Kleenex (for removing the surplus product) 1st strip | "Excess"/Dose nonabsorbed |
| Stratum corneum (2-15 strips max) | Balance of masses |
| Epidermis Dermis | Total Skin  Total penetration |
| Receiving Liquid | Dose absorbed |
| Analyses | LC/UV and LC/MS |
| Quantification limit | 1 ng/ml |

The amount of active agent in each compartment at each time was determined by LC/UV or by LC/MS. The bioanalysis method was validated so as to detect at least 0.1% of the dose applied in each compartment.

Figure 2:
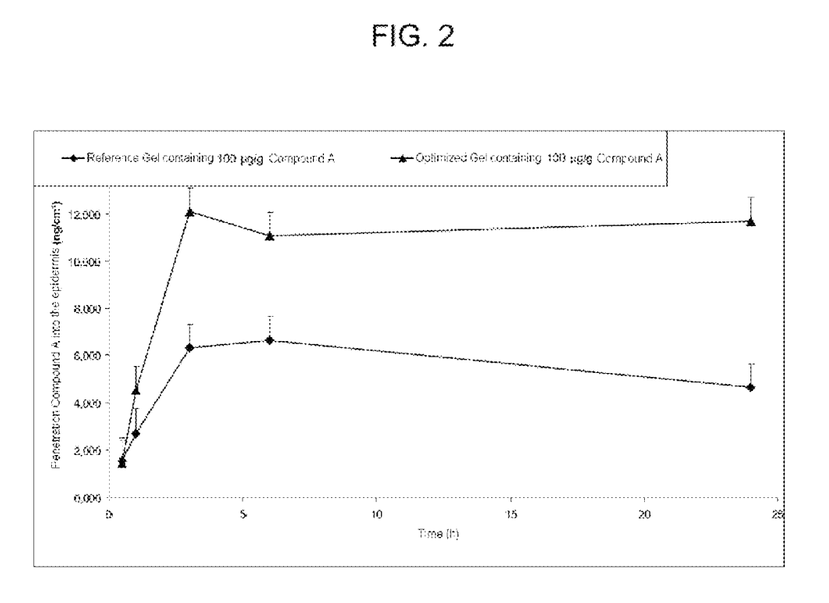

In this type of study, the parameters retained are:
 a. The profile of the kinetics of penetration into the epidermis (qualitative data).
 b. The initial rate of the penetration into the epidermis.
 c. The maximum amount penetrated into the epidermis.
 a. Profile of the Kinetics of Penetration into the Epidermis—FIG. 2:

The compound A release kinetics obtained for the optimized gel (example 3) shows a steep initial slope, followed by a maximum during which the penetration of compound A no longer increases over time. The reference formula (gel) shows the same profile with a rapid release over the first hours, with a plateau then being reached.

As seen in section 1 ("Single time" cutaneous penetration study), these two formulae have penetration levels at 16 h which are different; the penetration of compound A into the epidermis after application of the optimized gel (example 3) tends to be greater than that obtained after application of the reference gel.

b. Initial Rate of the Kinetics:
The value of the initial rate of the kinetics or slope over the first three hours is 4.12 ng/cm²/h.
 c. Maximum Amount in the Epidermis:
The maximum amount in the epidermis is 12.07 ng/cm².

Example 4

Cosmetic Study of Improved Feel

Tests for Improved Feel:

In order to obtain an acceptable feel for acne (non-greasy, non-tacky) while at the same time keeping good solubility of compound A in the formula, tests introducing ST-cyclomethicone 5 were carried out, in the knowledge that ST-cyclomethicone 5NF is a nonsolvent of compound A and that this addition may therefore cause recrystallization of compound A:

| ST-Cyclomethicone 5NF | 0% | 2% | 5% |
|---|---|---|---|
| Feel | Tacky feel | Acceptable feel | Acceptable feel |
| Recrystallization of COMPOUND A | No recrystallization | No recrystallization | Recrystallization |

These tests allowed us to optimize the amount of ST-cyclomethicone 5NF at 2% in order to obtain a cosmetically acceptable feel.

The invention claimed is:

1. A pharmaceutical composition comprising at least one active agent represented by a compound of general formula (I)

wherein
- $R_1$ is a hydrogen atom, an alkyl radical having from 1 to 4 carbon atoms or a —$CF_3$ radical;
- $R_2$ is a hydrogen atom, an alkyl or alkoxy radical having from 1 to 4 carbon atoms or a chlorine atom;
- $R_3$ is a hydrogen atom, or a linear or branched alkyl or alkoxy radical having from 1 to 10 carbon atoms, optionally substituted with a methoxy group;
- $R_4$ is a hydrogen atom or an alkyl radical having from 1 to 3 carbon atoms;
- $R_5$ is a hydrogen atom or an alkyl radical having from 1 to 3 carbon atoms;
- or else $R_4$ and $R_5$ form, together with the —N—C(=Y)— bond, a ring of pyrrolidine, pyrrolidinone, piperidine or piperidinone ring;
- Y represents two hydrogen atoms or a heteroatom;
- Ar represents a 1,4-phenyl, 2,5-pyridyl, 5,2-pyridyl or 2,5-thiophenyl ring;
- X represents a C—C single bond or an oxygen atom optionally substituted with an alkyl or alkylamine chain;

A represents a hydrogen atom or the formula below:

wherein
- Q is an oxygen atom or the —NH— bond;
- $R_6$ represents a hydrogen atom, an alkyl radical having from 1 to 6 carbon atoms, a cycloalkyl radical having from 3 to 6 carbon atoms, or a —$C(O)CH_2$ or —$C(O)CH_2CH_3$ radical;
- $R_7$ and $R_7'$ represent, independently of one another, a hydrogen atom or a hydroxyl group, on the condition that $R_7$ and $R_7'$ are not simultaneously a hydroxyl group;
- n is 0, 1, 2, 3, 4 or 5;

water, at least one gelling agent, at least one hydrophilic solvent and at least one hydrophilic cosolvent, wherein the compound of formula (I) is soluble in the hydrophilic solvent and the hydrophilic cosolvent, and wherein the hydrophilic solvent is selected from the group consisting of methylpyrrolidone, ethoxydiglycol, benzyl alcohol, polyethylene glycol, phenoxyethanol, ethanol, and mixtures thereof.

2. The composition as claimed in claim 1, wherein the compound of general formula (I) is defined such that:
- $R_1$ is a hydrogen atom, a t-butyl radical or an i-propyl radical;
- $R_2$ is a hydrogen atom, a t-butyl radical or an i-propyl radical;
- $R_3$ is a hydrogen atom or an ethyl radical;
- $R_4$ and $R_5$ are, independently of one another, a methyl or ethyl radical or else together form a pyrrolidine ring; and
- A is as defined previously, wherein $R_6$ represents a hydrogen atom, an i-propyl radical or a t-butyl radical, a cycloalkyl radical having from 3 to 6 carbon atoms, or a —$C(O)CH_2$ or —$C(O)CH_2CH_3$ radical.

3. The composition as claimed in claim 1, wherein the compound is 3"-tert-butyl-4'-(2-hydroxyethoxy)-4"-pyrrolidin-1-yl[1,1';3',1"]terphenyl-4-carboxylic acid.

4. The composition as claimed in claim 1, wherein the composition is an aqueous-glycolic gel in which the active agent is solubilized.

5. The composition as claimed in claim 1, wherein the gelling agent is selected from the group consisting of: polymers of vegetable origin, gums, pectins, cellulose, polymers of microbiological origin, and gelling polymers of synthetic origin.

6. The composition as claimed in claim 1, wherein the hydrophilic solvent is phenoxyethanol, ethanol or a mixture of phenoxyethanol and ethanol.

7. The composition as claimed in claim 1, wherein the cosolvent is a glycol.

8. The composition as claimed in claim 1, wherein the composition also comprises one or more additives selected from the group consisting of:
- one or more preserving agents;
- one or more agents for improving the properties of the formulae on application;
- one or more chelating agents;
- one or more antioxidants; and
- one or more soothing agents and/or anti-irritants.

9. The composition as claimed in claim 1, wherein the composition comprises the following ingredients:
from 0.00001% to 1% by weight of 3"-tert-butyl-4'-(2-hydroxyethoxy)-4"-pyrrolidin-1-yl[1,1';3',1"]terphenyl-4-carboxylic acid,
water,
from 0.005% to 10% by weight of gelling agent,
from 0.2% to 50% by weight of hydrophilic solvent,
from 2% to 50% by weight of cosolvent, and
optionally, from 0 to 15% by weight of additives.

10. The composition as claimed in claim 1, wherein a maximum amount of the active agent absorbed in the dermis and the epidermis 16 hours after application is from 5 $ng/cm^2$ to 15 $ng/cm^2$.

11. The composition as claimed in claim 1, wherein a maximum amount of the active agent absorbed in the epidermis is obtained from 1 to 6 hours after application.

12. The composition as claimed in claim 1, wherein the composition is provided in the form of a medicament.

13. The composition as claimed in claim 5, wherein the polymer of microbiological origin is xanthan gum.

14. The composition as claimed in claim 13, wherein the gelling agent is selected from the group consisting of:
acrylate/C10-30 alkyl acrylate crosspolymers,
polyacrylamides,
polyacrylamide/isoparaffin C13-14/laureth-7 mixtures,
carbomers,
polysaccharides,
aluminum magnesium silicates,
acrylic polymers coupled to hydrophobic chains,
modified starches, and
carrageenans.

15. The composition as claimed in claim 14, wherein the polyacrylamide is a sodium acrylamide/acryloyldimethyl taurate copolymer/isohexadecane/polysorbate 80 mixture.

16. The composition as claimed in claim 14, wherein the polysaccharides are selected from the group consisting of xanthan gum, gellan gum guar gum, and cellulose.

17. The composition of claim 16, wherein the cellulose is selected from the group consisting of microcrystalline cellulose, sodium carboxymethylcellulose, hydroxypropylmethylcellulose, hydroxyethylcellulose, and sodium carboxymethylcellulose.

18. The composition as claimed in claim 7, wherein the glycol is selected from the group consisting of propylene glycol, dipropylene glycol, and mixtures thereof.

19. The composition as claimed in claim 8, wherein the one or more preserving agents is selected from the group consisting of methyl paraben, propyl paraben, benzalkonium chloride, phenoxyethanol, benzyl alcohol, potassium sorbate, benzoic acid, 2-bromo-2-nitropropane-1,3-diol, chlorhexidine, chlorocresol, ethyl alcohol and diazolidinylurea.

20. The composition of claim 8, wherein the one or more agents for improving the properties of the formulae on application is cyclomethicone or dimethicone.

21. The composition as claimed in claim 8, wherein the one or more chelating agents is selected from the group consisting of an EDTA (ethylenediaminetetraacetic acid) and salts thereof, dihydroglycerol, citric acid, tartaric acid and gluconolactone.

22. The composition as claimed in claim 8, wherein the one or more antioxidants is selected from the group consisting of vitamin E and vitamin C.

23. The composition as claimed in claim 22, wherein the vitamin E is DL-alpha-tocopherol or tocopheryl acetate.

24. The composition as claimed in claim 22, wherein the vitamin C is ascorbyl palmitate or butylhydroxytoluene.

25. The composition as claimed in claim 8, wherein the one or more soothing agents and/or anti-irritants is selected from the group consisting of PPG-12/SMDI copolymer, glycyrrhetinic acid, hyaluronic acid or its sodium hyaluronate form, and allantoin.

26. Then composition as claimed in claim 9, wherein the amount of the 3"-tert-butyl-4'-(2-hydroxyethoxy)-4"-pyrrolidin-1-yl[1,1';3',1"]terphenyl-4-carboxylic acid is from 0.0001% to 0.1% by weight.

27. The composition as claimed in claim 26, wherein the amount of the 3"-tert-butyl-4'-(2-hydroxyethoxy)-4"-pyrrolidin-1-yl[1,1';3',1"]terphenyl-4-carboxylic acid is from 0.001% to 0.1% by weight.

28. The composition as claimed in claim 9, wherein the amount of the gelling agent is from 1% to 4% by weight.

29. The composition as claimed in claim 9, wherein the amount of the hydrophilic solvent is from 0.5% to 30% by weight.

30. The composition as claimed in claim 9, wherein the amount of cosolvent is from 10% to 40% by weight.

31. The composition as claimed in claim 9, wherein the amount of the additives is from 0.1% to 10% by weight.

32. The composition as claimed in claim 1, wherein Y represents a heteroatom selected from oxygen or sulfur.

33. The composition as claimed in claim 14, wherein the acrylic polymer coupled to hydrophobic chains is PEG-150/decyl/SMDI copolymer.

34. The composition as claimed in claim 14, wherein the modified starch is a modified potato starch.

35. The composition as claimed in claim 14, wherein the carrageenan is divided up into four major families: κ, λ, β, ω.

36. The composition of claim 5, wherein the cellulose is selected from the group consisting of microcrystalline cellulose, sodium carboxymethylcellulose, hydroxypropylmethylcellulose, hydroxyethylcellulose and sodium carboxymethylcellulose.

37. A method of treating a pathological condition, the method comprising administering to an individual subject in need thereof an effective amount of the composition as claimed in claim 1, wherein the pathological condition is selected from the group consisting of:
common acne, comedonal acne, polymorphic acne, acne rosacea, nodulocystic acne, acne conglobata, senile acne or secondary acne;
ichthyosis, ichthyosiform conditions, lamellar ichthyosis, Darier's disease, palmoplantar keratoderma, leukoplakia, *pityriasis rubra* pilaris and leukoplakiform conditions, cutaneous or mucosal (buccal) lichen;
dermatological conditions with an inflammatory immunoallergic component, with or without a cell proliferation disorder;
skin disorders caused by exposure to UV radiation, photo-induced or chronological skin aging, actinic keratoses and pigmentations, or pathological conditions associated with chronological or actinic aging;
common warts, flat warts, molluscum contagiosum, epidermodysplasia verruciformis, or oral or florid papillomatoses;
immune dermatoses;
stigmata of epidermal and/or dermal atrophy induced by local or systemic corticosteroids, or any other form of cutaneous atrophy;
healing disorders, or for repairing stretch marks, or for promoting healing;
conditions of fungal origin at the cutaneous level;
pigmentation disorders; and cutaneous or mucosal cancerous or precancerous conditions.

38. The method as claimed in claim 37, wherein the dermatological condition with an inflammatory immunoallergic component is selected from cutaneous, mucosal or ungual psoriasis, psoriatic arthritis, atopic dermatitis and eczema.

39. The method as claimed in claim 37, wherein the pathological condition associated with chronological or actinic aging is selected from xerosis, pigmentations or wrinkles.

40. The method as claimed in claim 37, wherein the immune dermatosis is lupus erythematosus.

41. The method as claimed in claim 37, wherein the collagen disease is scleroderma.

42. The method as claimed in claim 37, wherein the condition of fungal origin at the cutaneous level is tinea pedis or tinea versicolor.

43. The method as claimed in claim 37, wherein the pigmentation is hyperpigmentation, melasma, hypopigmentation or vitiligo.

44. The method as claimed in claim 37, wherein the cutaneous or mucosal cancerous or precancerous condition is selected from the group consisting of tinic keratoses, Bowen's disease, in-situ carcinomas, keratoacanthomas, basal cell carcinoma (BCC), squamous cell carcinoma (SCC) and cutaneous lymphomas.

45. The method as claimed in claim 44, wherein the cutaneous lymphoma is T lymphoma.

46. A method of treating a pathological condition, the method comprising administering to an individual subject in need thereof an effective amount of the composition as claimed in claim 1, wherein the pathological condition is selected from the group consisting of lupus erythematosus, bullous immune diseases, and collagen diseases.

47. The method as claimed in claim 37, wherein the secondary acne is solar acne, acne medicamentosa or occupational acne.

* * * * *